United States Patent
Tsuda

(10) Patent No.: US 7,211,678 B2
(45) Date of Patent: May 1, 2007

(54) STABLE CRYSTALS OF PYRROLE COMPOUND

(75) Inventor: Masami Tsuda, Hiroshima (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 0 days.

(21) Appl. No.: 10/471,442

(22) PCT Filed: Mar. 13, 2002

(86) PCT No.: PCT/JP02/02331

§ 371 (c)(1),
(2), (4) Date: Sep. 10, 2003

(87) PCT Pub. No.: WO02/072546

PCT Pub. Date: Sep. 19, 2002

(65) Prior Publication Data

US 2005/0261161 A1    Nov. 24, 2005

(30) Foreign Application Priority Data

Mar. 14, 2001    (JP) ............................. 2001-072405

(51) Int. Cl.
*C07D 207/00* (2006.01)
(52) U.S. Cl. .................................................. 548/558
(58) Field of Classification Search ................ 548/558; 514/408

See application file for complete search history.

(56) References Cited

U.S. PATENT DOCUMENTS 5,998,459 A * 12/1999 Tsuda et al. ................ 514/408
6,172,102 B1 * 1/2001 Tsuda et al. ................ 514/422
6,353,016 B1 * 3/2002 Tanaka et al. .............. 514/422

FOREIGN PATENT DOCUMENTS

EP    0 842 923 A1    5/1998

OTHER PUBLICATIONS

Nicholas D. Cheronis, 1958, "Semimicro Experimental Organic Chemistry", Chapter 5.*
Brittain, H. G., polymorphism, in Pharmaceutical Solids, Drugs and the Pharmaceutical Science; 1999, V. 95, pp. 348-361.*
Brittain, H. G., polymorphism in Pharmaceutical Solids, Drugs and the Pharmaceutical Science; 1999, V. 95, pp. 227-228, 252-256, and 275-276.*

* cited by examiner

Primary Examiner—Joseph K. McKane
Assistant Examiner—Robert Shiao
(74) Attorney, Agent, or Firm—Greenberg Traurig LLP; Gerard F. Diebner

(57) ABSTRACT

The present invention is constituted with crystal of 2-amino-3-cyano-4-methyl-5-(2-fluorophenyl)pyrrole, which show diffraction peaks at diffraction angles ($2\theta \pm 0.2$ degree) of 10.3 degree, 14.3 degree, 15.5 degree, 15.9 degree, 25.1 degree and 25.7 degree in a powder X-ray diffraction spectrum, and also show absorption peaks at wavenumbers ($cm^{-1}$, $\pm 0.2\%$) of 3373, 3322, 2201, 762, 687 and 640 in an infrared absorption spectrum.

The crystal of the present invention is superior in stability and is useful as a pharmaceutical bulk.

1 Claim, 5 Drawing Sheets

STABLE CRYSTALS OF PYRROLE COMPOUND

This application is a 371 of PCT/JP02/02331 filed on Mar. 13, 2002.

TECHNICAL FIELD

The present invention relates to a crystal of 2-amino-3-cyano-4-methyl-5-(2-fluorophenyl)pyrrole, which is useful for the treatment of pollakiuria or urinary incontinence.

BACKGROUND ART

WO96/40634 describes that 2-amino-3-cyano-4-methyl-5-(2-fluorophenyl)pyrrole (hereinafter referred to as the pyrrole compound) has excellent urinary bladder capacity increasing activity and is useful for the treatment of pollakiuria or urinary incontinence. Also Examples 5-(1) and 5-(2) of the above publication describe that crystal (hereinafter referred to as type-II crystal) of the pyrrole compound by recrystallizing the pyrrole compound from a mixed solvent (1:1) of benzene and n-hexane, or benzene.

DISCLOSURE OF THE INVENTION

It is necessary to provide drugs having high quality and the same quality so that fixed actions and effects can be ordinary expected. Therefore, there can be required, as an active ingredient of drugs, those which show fixed properties and also have high stability and a form having excellent shelf life.

Also with respect to the pyrrole compound mentioned above, it has been required to find those which show fixed properties suited for the manufacture of drugs and also have a stable form.

Type-II crystal had such a problem that the quality deteriorates in a grinding step in the manufacture of a pharmaceutical preparation because of poor stability.

The inventors of the present invention have intensively studied for the purpose of obtaining a crystal which is stable in the grinding step and can be practically used in the manufacture of a pharmaceutical preparation.

As a result, they have found a crystal which is more stable than conventional type-II crystal (hereinafter referred to as type-I crystal), and thus the present invention has been completed.

Namely, the present invention provides stable type-I crystal of the pyrrole compound. Type-I crystal is characterized by showing diffraction peaks at diffraction angles (2θ±0.2 degree) of 10.3 degree, 14.3 degree, 15.5 degree, 15.9 degree, 25.1 degree and 25.7 degree in a powder X-ray diffraction spectrum. Among the peaks, peaks at 10.3 degree, 14.3 degree, 15.9 degree and 25.7 degree are more characteristic.

Also type-I crystal is characterized by showing absorption peaks at wavenumbers ($cm^{-1}$, ±0.2%) of 3373, 3322, 2201, 762, 687 and 640 in an infrared absorption spectrum (KBr method).

Type-I crystal of the present invention can be obtained by recrystallizing in the following manner.

(1) Dissolution Step

The pyrrole compound is dissolved in an organic solvent by heating. As the organic solvent, aromatic hydrocarbon solvents such as toluene, xylene and ethylbenzene are preferable, and toluene is particularly preferable. The amount of the organic solvent is preferably 20 to 40 times by weight, more preferably 20 to 30 times by weight, and particularly preferably 22 times by weight, larger than that of the pyrrole compound. The heating temperature varies depending on the kind and amount of the organic solvent, but is preferably from 60 to 80° C., and particularly preferably about 75° C. This step is preferably carried out in a flow of an inert gas such as nitrogen or argon.

The pyrrole compound to be used can be produced by the method described in Example 5-(1) or Example 5-(2) on pages 43–44 of WO96/40634 and is preferably subjected to an active carbon treatment in advance. The pyrrole compound may be in any crystalline or amorphous form.

To remove insolubles, the solution may be filtered. To prevent the precipitation of crystals during the filtration, filtration is preferably carried out under pressure using a funnel equipped with a heating device. In case the precipitation of crystals is observed in the filtrate, the filtrate is dissolved again by reheating after the filtration.

(2) Cooling Step

The solution is cooled to precipitate crystals. This step is preferably carried out in a flow of an inert gas such as nitrogen or argon using a crystallizer equipped with a heating function for dissolving the precipitate and a stirring function for cooling.

The cooling temperature is preferably from 2 to 20° C., and particularly preferably from 5 to 10° C. After reaching the cooling temperature, the crystallization time is preferably from 30 minutes to 2 hours, and particularly preferably 1 hour. When the solution is cooled to a temperature ranging from 60 to 65° C., type-I seed crystal is preferably added. Type-I seed crystal can be obtained, for example, by operating as described in Example 1 described hereinafter. The amount of type-I seed crystal is preferably from 0.3 to 1.0% by weight based on the pyrrole compound used. The cooling rate is preferably from 0.5 to 1.5° C./min. in case of adding type-I seed crystal, while the cooling rate is preferably 0.5° C./min. in case of adding no type-I seed crystal.

(3) Crystal Collection and Drying Step

The precipitated crystals are collected by a known means such as filtration or centrifugation and then dried. Drying can be carried out under reduced pressure or over a desiccant. Particularly, drying is preferably carried out under reduced pressure, for example, of 10 mmHg or less at 20 to 60° C. for 1 to 48 hours.

As shown in Examples and Test Examples described hereinafter, type-I crystal of the present invention is stable in grinding test as compared with type-II crystal as conventional crystal, and also has good appearance under an electron microscope. Therefore, type-I crystal of the present invention can be advantageously used as a pharmaceutical bulk in the manufacture of a pharmaceutical preparation.

BEST MODE FOR CARRYING OUT THE INVENTION

The present invention will be described in more detail by way of the following Reference Examples, Examples and Test Examples of the crystal of the present invention.

A powder X-ray diffraction spectrum was measured by RAD-2B (target: Cu, voltage: 40 kV, current: 20 mA, scan speed: 4 degree/min.) manufactured by Rigaku Corporation. Also an infrared absorption spectrum was measured by a KBr method using a FT-IR device, Model 1640, manufactured by PerkinElmer, Inc.

REFERENCE EXAMPLE 1

Type-II Crystal of 2-amino-3-cyano-4-methyl-5-(2-fluorophenyl)pyrrole

The crystal was produced in accordance with the method described in Example 5-(1) on page 43 of WO96/40634.

1-(2-Fluorophenyl)-1-acetamido-2-propanone (3.13 g) and malononitrile (1.49 g) were dissolved in methanol (15 ml) and the solution was stirred under ice-cooling. Then, 55% aqueous solution of potassium hydroxide was added to the above solution to adjust to pH 10. The reaction solution was then warmed and stirred at 55–60° C. for 0.5 hours. After cooling, the reaction solution was poured into iced water and the resulting crystals were collected by filtration. This crude crystalline product was recrystallized from a mixed solvent of methanol and water and, further, from benzene to obtain type-II crystal (0.72 g). Melting point: 117 to 118° C.

Figure 2:
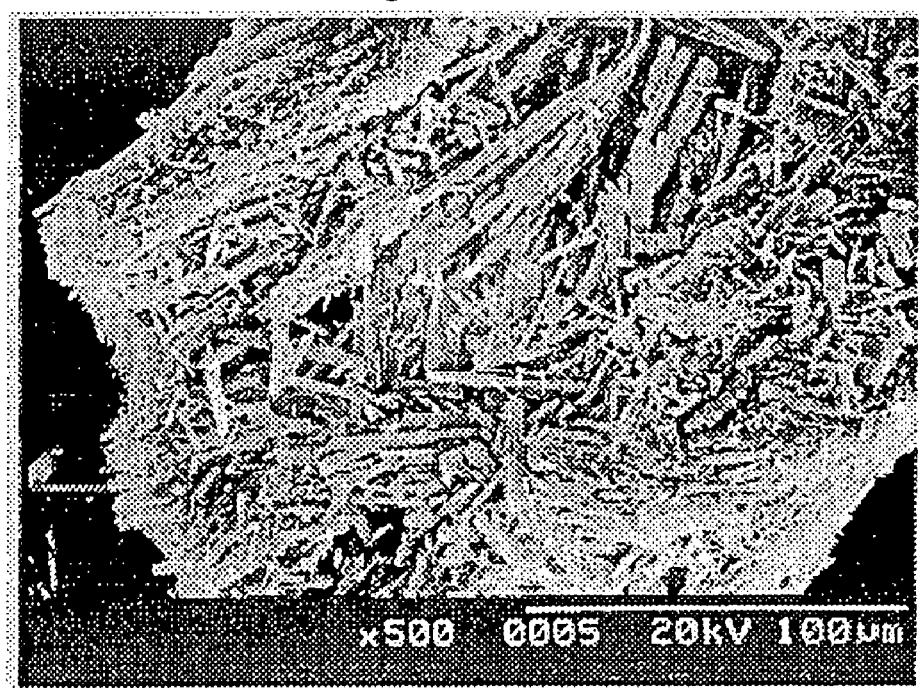
FIG. 2 is a scanning electron microscopy image taken at 500 times magnification of type-II crystal of the pyrrole compound.

A scanning electron microscopy image of type-II crystal is shown in FIG. 2. Type-II crystal has non-uniform crystal diameter and also has irregularity on the surface thereof.

Figure 4:
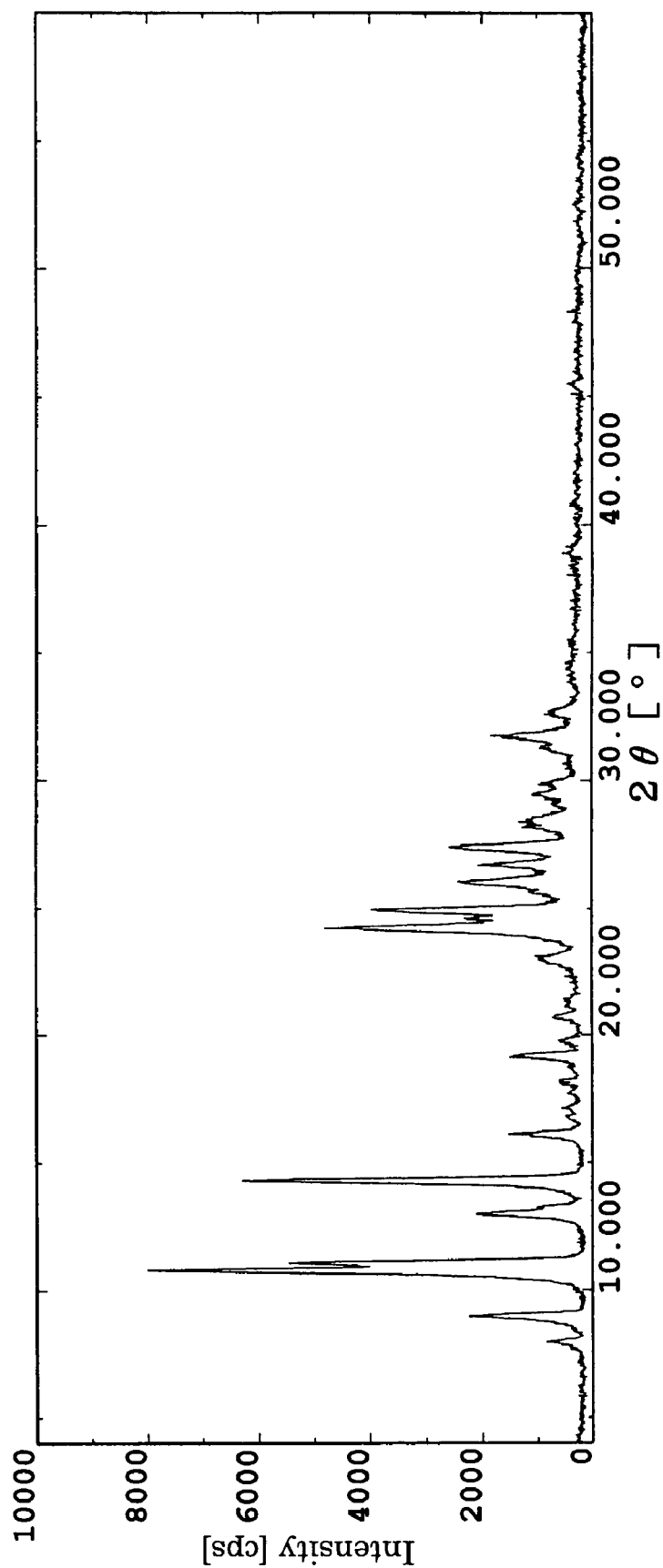
FIG. 4 is a powder X-ray diffraction spectrum chart of type-II crystal of the pyrrole compound. The abscissa indicates a diffraction angle (2θ), while the ordinate indicates a peak intensity.

A powder X-ray diffraction spectrum chart is shown in FIG. 4. Type-II crystal shows diffraction peaks at diffraction angle (2θ+0.2 degree) of 10.8 degree, 11.1 degree, 14.3 degree, 24.2 degree and 24.9 degree.

Figure 8:
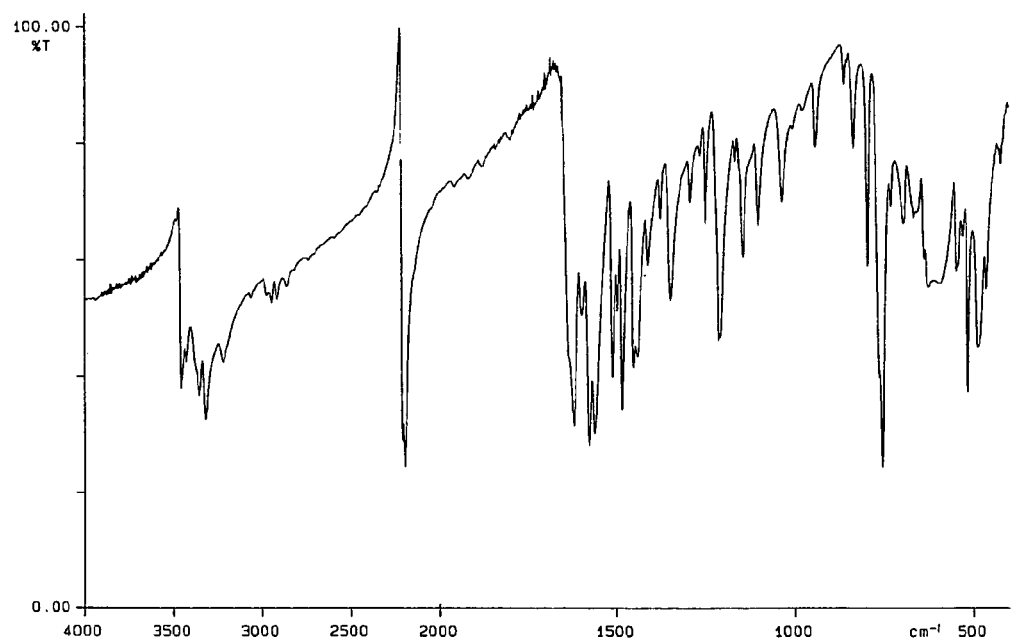
FIG. 8 is an infrared absorption spectrum chart of type-II crystal of the pyrrole compound. The abscissa indicates a wavenumbers ($cm^{-1}$), while the ordinate indicates a transmittance.

An infrared absorption spectrum chart is shown in FIG. 8. Type-II crystal shows absorption peaks at wavenumbers ($cm^{-1}$, ±0.2%) of 3318, 2210, 2194 and 753.

EXAMPLE 1

Type-I Seed Crystal of 2-amino-3-cyano-4-methyl-5-(2-fluorophenyl)pyrrole

To crude 2-amino-3-cyano-4-methyl-5-(2-fluorophenyl)pyrrole (24.0 g) produced in accordance with the method described in Reference Example 1, toluene (600 mL) was added, and the mixture was degassed and dissolved in a nitrogen gas flow by heating to 70° C. After the resulting solution was filtrated under pressure, the filtrate was transferred to a crystallizer. In a nitrogen gas flow, the precipitate was dissolved again by warming the filtrate at 75° C., and then cooled to 5° C. at a cooling rate of 0.5° C./min. while stirring at 100 rpm. The precipitated crystals were collected by filtration and dried to obtain type-I crystal (21.4 g). Melting point: 119 to 120° C.

Elemental analysis (for $C_{12}H_{10}FN_3$)

Calcd. (%) C, 66.97; H, 4.68; N, 19.52.

Found (%) C, 66.95; H, 4.38; N, 19.40.

Figure 1:
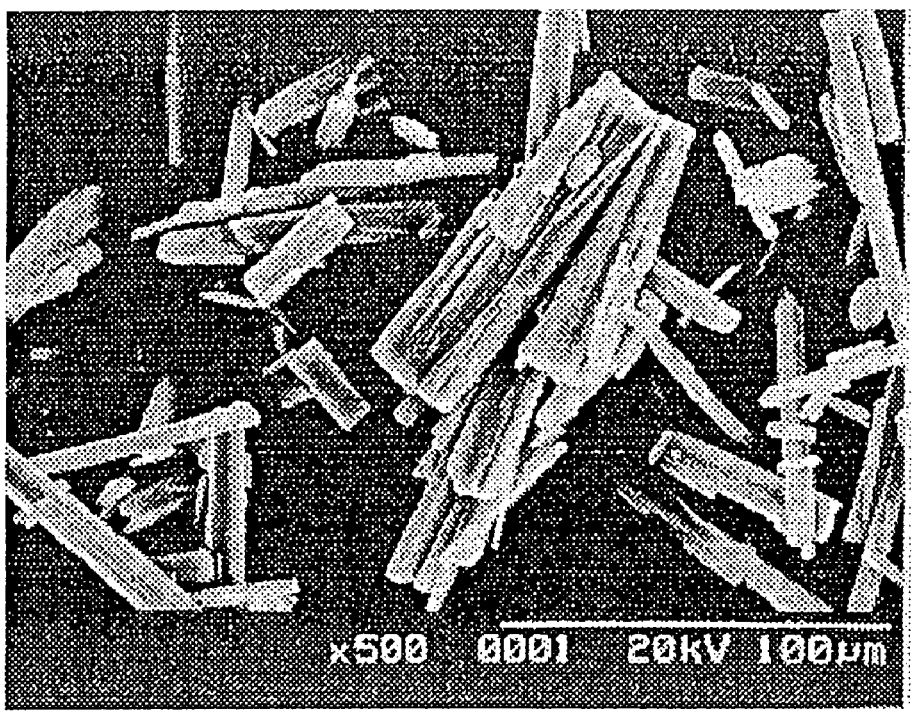
FIG. 1 is a scanning electron microscopy image taken at 500 times magnification of type-I crystal of the pyrrole compound.

A scanning electron microscopy image of type-I crystal is shown in FIG. 1. Type-I crystal is columnar crystal having excellently uniform shape.

Figure 3:
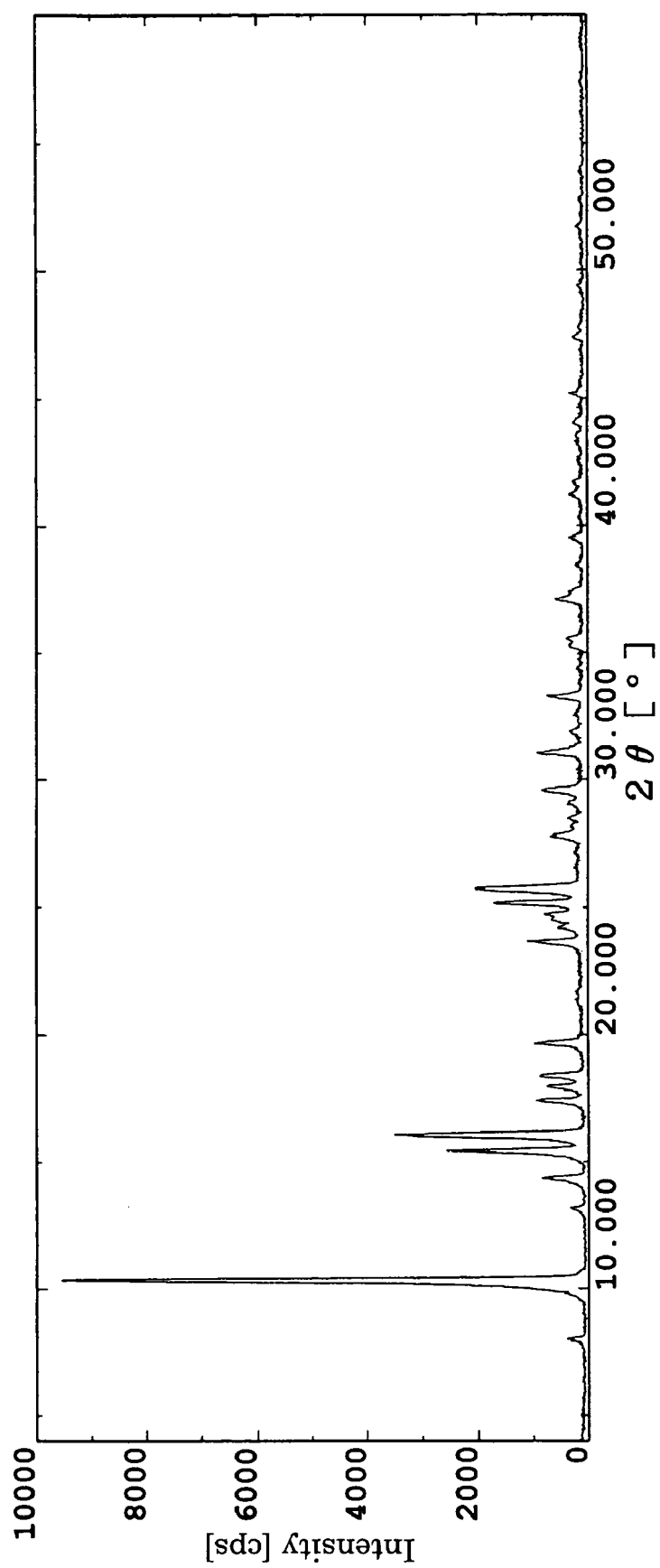
FIG. 3 is a powder X-ray diffraction spectrum chart of type-I crystal of the pyrrole compound. The abscissa indicates a diffraction angle (2θ), while the ordinate indicates a peak intensity.

A powder X-ray diffraction spectrum chart is shown in FIG. 3. Type-I crystal shows diffraction peaks at diffraction angles (2θ±0.2 degree) of 10.3 degree, 14.3 degree, 15.5 degree, 15.9 degree, 25.1 degree and 25.7 degree. Among the peaks, peaks at 10.3 degree, 14.3 degree, 15.9 degree and 25.7 degree are more characteristic.

Figure 7:
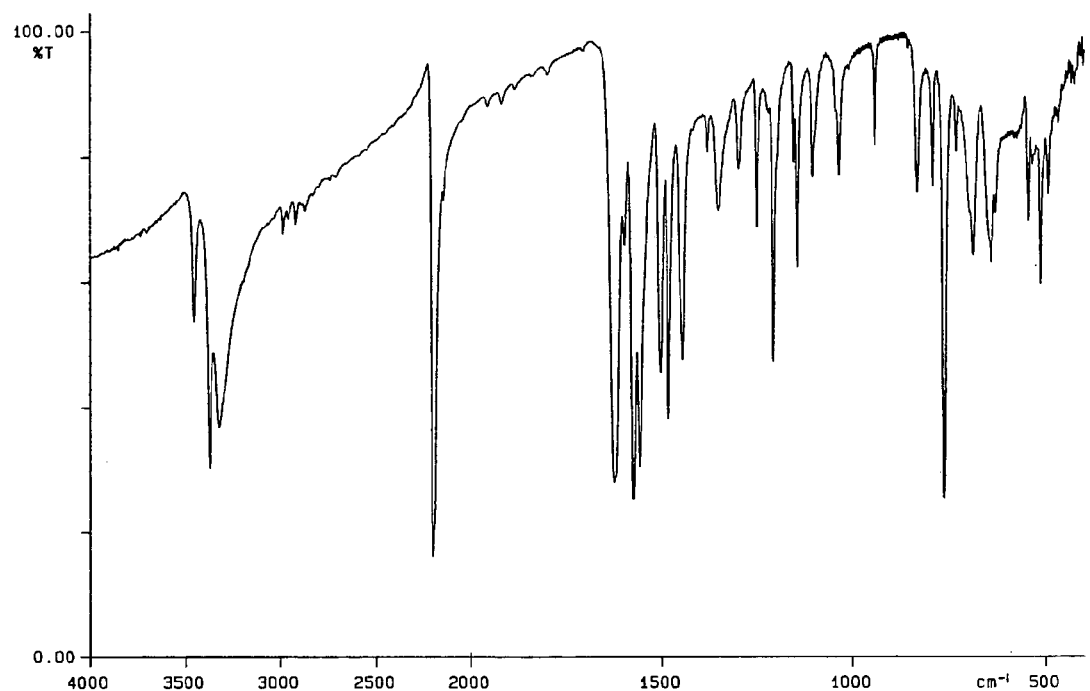
FIG. 7 is an infrared absorption spectrum chart of type-I crystal of the pyrrole compound. The abscissa indicates a wavenumbers ($cm^{-1}$), while the ordinate indicates a transmittance.

An infrared absorption spectrum chart is shown in FIG. 7. Type-I crystal shows absorption peaks at wavenumbers ($cm^{-1}$, ±0.2%) of 3373, 3322, 2201, 762, 687 and 640.

EXAMPLE 2

Type-I Crystal of 2-amino-3-cyano-4-methyl-5-(2-fluorophenyl)pyrrole

To crude 2-amino-3-cyano-4-methyl-5-(2-fluorophenyl)pyrrole (24.0 g) produced in accordance with the method described in WO96/40634, toluene (600 mL) was added, and the mixture was degassed and then dissolved by heating to 70° C. in a nitrogen gas flow. After the solution was filtered under pressure, the filtrate was transferred to a crystallizer. In a nitrogen gas flow, the precipitate was dissolved again by warming the filtrate at 75° C., and then cooled to 65° C. at a cooling rate of 1.0° C./min while stirring at 200 rpm. Seed crystals (120 mg) obtained in Example 1 were added to the solution, and the mixture was cooled to 5° C. at a cooling rate of 1.5° C./min and then cooled at 5° C. for 1 hour. The precipitated crystals were collected by filtration and dried to obtain type-I crystal (21.65 g). The physical constants of the resulting type-I crystal were in agreement with those of the type-I crystal obtained in Example 1.

TEST EXAMPLE 1

Dry Grinding Test

Type-I crystal (1 g) and type-II crystal (1 g) were respectively charged in a planet ball mill (manufactured by Fritsch Japan) and then grinded at 2480 rpm for 5 hours. The grinded crystals were evaluated by a powder X-ray spectrum.

Figure 5:
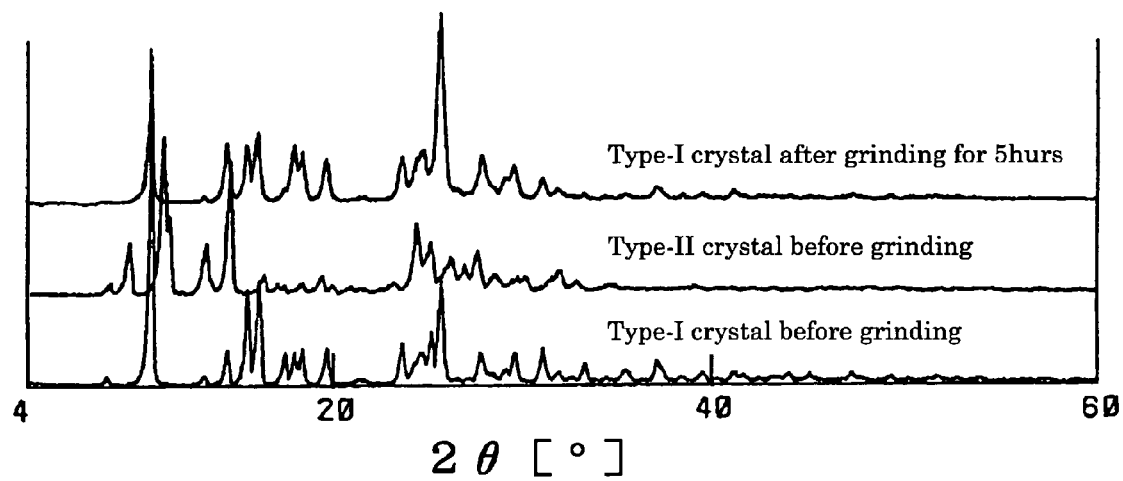
FIG. 5 is a powder X-ray diffraction spectrum chart in which a comparison is made between grinded type-I crystal and type-I and type-II crystals before grinding. The abscissa indicates a diffraction angle (2θ), while the ordinate indicates a peak intensity.

A comparison between grinded type-I crystal and type-I and type-II crystal before grinding is shown in FIG. 5.

Figure 6:
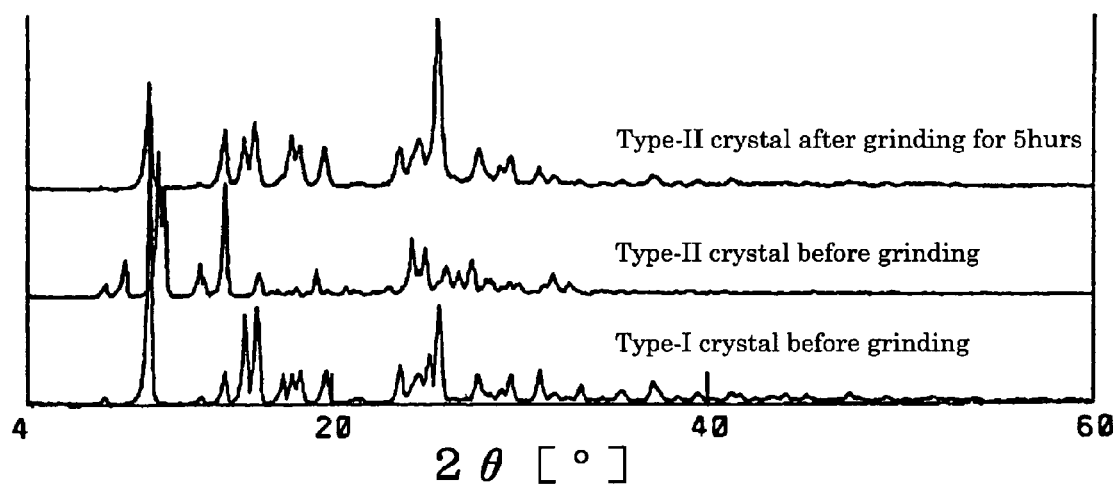
FIG. 6 is a powder X-ray diffraction spectrum chart in which a comparison is made between grinded type-II crystal and type-I and type-II crystals before grinding. The abscissa indicates a diffraction angle (2θ), while the ordinate indicates a peak intensity.

A comparison between grinded type-II crystal and type-I and type-II crystal before grinding is shown in FIG. 6.

No crystal transition was recognized in dry grinded type-I crystals, while transition of crystals into type-I crystal was recognized in dry grinded type-II crystal.

INDUSTRIAL APPLICABILITY

Type-I crystal of the present invention can be used as a pharmaceutical bulk in the manufacture of a pharmaceutical preparation because the crystals are stable to grinding as compared with type-II crystal.

The invention claimed is:

1. A type-I crystal of 2-amino-3-cyano-4-methyl-5-(2-fluorophenyl) pyrrole, which shows characteristic diffraction peaks at diffraction angles ($2\theta \pm 0.2$ degree) of 10.3 degree, 14.3 degree, 15.9 degree and 25.7 degree in a powder X-ray diffraction spectrum, which shows absorption peaks at wavenumbers (cm−1, ±0.2%) of 3373, 3322, 2201, 762, 687 and 640 in an infrared absorption spectrum.

* * * * *